(12) United States Patent
Zimmerman

(10) Patent No.: US 8,343,030 B2
(45) Date of Patent: Jan. 1, 2013

(54) HARMONIC AND OVERTONE AUDIO THERAPY FOR AUTISM SPECTRUM DISORDER (ASD) AND REGULATED EMOTIONAL AND PSYCHOLOGICAL DISORDERS

(76) Inventor: Clifford Neil Zimmerman, Roswell, GA (US)

(*) Notice: Subject to any disclaimer, the term of this patent is extended or adjusted under 35 U.S.C. 154(b) by 1449 days.

(21) Appl. No.: 11/553,129

(22) Filed: Oct. 26, 2006

(65) Prior Publication Data

US 2008/0101621 A1    May 1, 2008

(51) Int. Cl.
*A61M 21/00* (2006.01)
(52) U.S. Cl. ............................................ 600/28; 381/61
(58) Field of Classification Search ................ 600/9–15, 600/26–28; 128/897–898
See application file for complete search history.

(56) References Cited

U.S. PATENT DOCUMENTS

| | | | | |
|---|---|---|---|---|
| 2,241,027 A | * | 5/1941 | Bumstead | 84/639 |
| 3,916,754 A | * | 11/1975 | Thiel | 84/402 |
| 4,248,119 A | * | 2/1981 | Yamada | 84/637 |
| 5,501,130 A | | 3/1996 | Gannon et al. | |
| 2005/0192514 A1 | | 9/2005 | Kearby et al. | |

OTHER PUBLICATIONS

Stephen M. Edelson, Ph.D., Basic Information About Auditory Integration Training (AIT), Center for the Study of Autism, Salem, Oregon, 1995.
Gomes E, Rotta NT, Pedroso FS, Sleifer P, Danesi MC, Auditory Hypersensitivity in Children and Teenagers With Autistic Spectrum Disorder, Arq Neuropsiquiatr (Sep. 2004), PubMed Abstract.
Moller AR, Kern JK, Grannemann B., Are the Non-Classical Auditory Pathways Involved in Autism and PDD?, Neurol Res (Sep. 2005); PubMed Abstract.
Bettison S., The Long-Term Effects of Auditory Training on Children With Autism, J. Autism Dev Disord. (Jun. 1996), PubMed Abstract.
Sinha Y, Silove N, Wheeler D, Williams K., Auditory Integration Training and Other Sound Therapies for Autism Spectrum Disorders, Cochrane Database Syst Rev. (2004), PubMed Abstract.
Thomson Healthcare, Sound Therapy (2004), http://www.pdrhealth.com/coontent/natural_medicine/chapters/201460.shtml.

* cited by examiner

*Primary Examiner* — Charles A Marmor, II
*Assistant Examiner* — Carrie R Dorna
(74) *Attorney, Agent, or Firm* — Thomas Horstemeyer, LLP

(57) ABSTRACT

A therapeutic method and sound recording including sounding a first harmonic interval for a first duration of at least approximately one minute; and sounding a second harmonic interval for a second, consecutive duration for at least approximately one minute. The first and second harmonic intervals may be just intervals and/or fifths, such as Perfect 5ths (P5). The first duration may overlap with the second duration in order to sound a Major Seventh (M7) chord. The first duration may be approximately twenty minutes long or longer, the second duration may be approximately ten minutes long or longer, and the overlap between the first and second duration may be approximately ten minutes long or longer.

18 Claims, 1 Drawing Sheet

HARMONIC AND OVERTONE AUDIO THERAPY FOR AUTISM SPECTRUM DISORDER (ASD) AND REGULATED EMOTIONAL AND PSYCHOLOGICAL DISORDERS

TECHNICAL FIELD

The subject matter disclosed here generally relates to sensory therapies, and, more particularly, to harmonic and overtone audio therapy for treating persons with Autism Spectrum Disorder, including Asperger's Syndrome and/or related emotional and physiological disorders.

BACKGROUND OF THE INVENTION

Various healing traditions, medical and otherwise, have used sound to help heal the body. For example, one of the most common therapeutic uses of sound is in music therapy. Music has been clinically proven to reduce heart rates, blood pressure, pain, anxiety, and to otherwise improve patients' moods. The lower the frequency, the more harmonics and overtones are produced; the resulting "sound bath" is the hallmark of key therapeutic benefits.

The Berard Auditory Integration Training Method, or AIT, is a form of audio therapy that uses processed music in which the low and high frequencies have been removed at random. The patient typically listens to two, half-hour sessions each day for a period of ten days. Proponents of the Berard Method claim that it can help with various developmental disorders.

Various studies have investigated these and other auditory aspects of autistic spectrum disorders. For example, in "Are the Non-Classical Auditory Pathways Involved in Autism and PDD?," Neurol Res. September 2005; 27(6):625-9, the authors conclude that some individuals with autism appear to have an abnormal cross-modal interaction between the auditory and the somatosensory systems. As only the non-classical "extralemniscal" ascending auditory pathways receive somatosensory input, the presence of cross-modal interaction in autistic individuals is reported to be a sign that autism is associated with abnormal involvement of the non-classical auditory pathways. This implies that sensory information is processed by different populations of neurons in non-autistic and autistic individuals.

In "Auditory Hypersensitivity in Children and Teenagers with Autistic Spectrum Disorder," Arg Neuropsiquiatr September 2004; 62 (313): 797-801, the authors conclude that behavioral manifestations to sounds are not associated with the hypersensitivity of auditory pathways in autistic individuals. Instead, autistic individuals appear to have difficulties with upper processing as may be involved in the limbic system.

In "The Long-Term Effects of Auditory Training on Children with Autism," J. Autism Dev. Discord. June 1997: 27(e): 347-8, the authors found that verbal and performance I.Q. increased significantly after three to twelve months of auditory training. Their findings suggested that some aspects of both auditory training and listening to selected unmodified music has a beneficial effects on children with autism and sound sensitivity.

Based upon these and other investigations, various audio therapies have been proposed for individuals with Autistic Spectrum disorders, including Asperger's Syndrome, and/or other, emotional and physiological disorders.

SUMMARY OF THE INVENTION

The technology disclosed here generally relates to a therapeutic method including the steps of sounding a first harmonic interval for a first duration of at least approximately one minute, and sounding a second harmonic interval for a second, consecutive duration for at least approximately one minute. For example, the first and second harmonic intervals may be Major thirds, minor thirds, Major sevenths and fifths, such as Perfect Fifths and the first duration may overlap with the second duration. A Perfect Fifth (P5) is also referred to as an Inverted Fourth. In some embodiments, the overlap of the first and second duration may sound a Major Seventh chord. For example, the first duration may be approximately twenty minutes long or longer, the second duration approximately ten minutes long or longer, and the overlap between the first and second duration may be approximately ten minutes long or longer. In another embodiment, the technology disclosed here may relate to a therapeutic sound recording including similar features.

BRIEF DESCRIPTION OF THE DRAWINGS

Many aspects of the technology disclosed here can be better understood with reference to the following drawings. The components in the drawings are not necessarily to scale, instead emphasis is being placed upon illustrating the principles of this technology. Moreover, in the drawings, like reference numerals designate corresponding parts throughout the several views.

DETAILED DESCRIPTION

Figure 1:
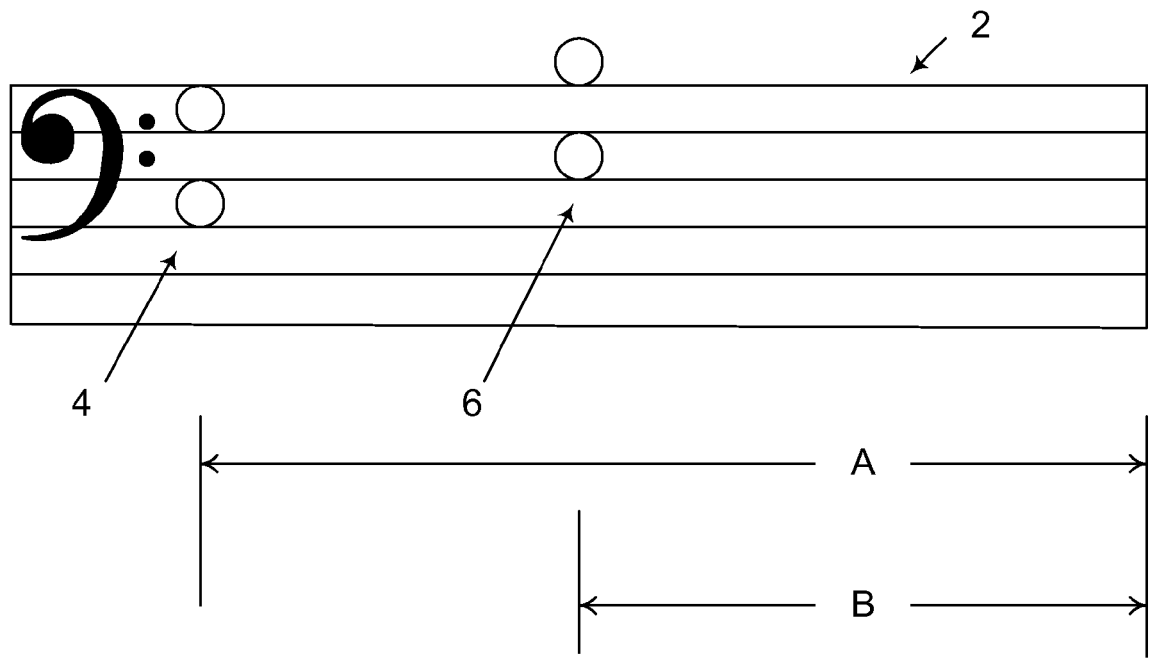
FIG. 1 is a musical staff (bass clef), illustrating one embodiment of a therapeutic method.

FIG. 1 shows a musical staff illustration of one of several embodiments for a therapeutic method 2. Although a bass clef is illustrated in FIG. 1 other clefs may also be used. In FIG. 1, a first harmonic interval 4 is sounded for a first duration A, while a second harmonic interval 6 is sounded for a second duration B. In the illustrated exemplary embodiment, the time period for duration A is typically between approximately one and approximately twenty minutes, or longer, and the time period for duration B is between approximately one and approximately ten minutes, or longer. However, a variety of longer or shorter durations may also be used. Therapeutic benefits become cumulative over time.

For example, the durations may depend upon the mood and/or ability of the patient to comply with the treatment protocol. It is expected that most patients will be able to comply with relatively short treatment periods of two minutes for duration A and one minute for duration B. It is also expected that additional benefits will be provided to the patient who complies with a longer treatment period of up to 30 minutes for duration A and fifteen minutes for duration B. However, longer treatment periods may also be used depending upon the ability of the patient to comply.

The therapeutic method 2 illustrated in FIG. 1 is typically repeated at least daily in order to reinforce its beneficial effects for the patient. However, other re-treatment intervals may also be used including multiple times per day, or less than seven times per week.

In FIG. 1, the time period for the second duration B starts midway through the interval A and entirely overlaps with a portion of the duration time period for the first duration A. However, the time periods for duration A and consecutive duration B may also only partially overlap or not overlap at all. Furthermore, the duration B and/or the duration A may gradually change in volume, such as during an approximately ten second interval where the volume of duration B increases at the beginning of duration B.

According to the Wikipedia Encyclopedia, which is incorporated by reference here in its entirety, an interval is the distance in pitch between two notes, where pitch is the perception of frequency of the note or tone. Intervals may be harmonic (or vertical) if the two notes sound simultaneously, or melodic (or linear), if the notes sound successively. Although FIG. 1 illustrates harmonic intervals 4 and 6, melodic and/or partially melodic intervals may also be used, particularly when leading to a harmonic interval of longer duration.

The interval number of a note from a given tonic note is the number of staff positions enclosed within the interval. The name of any interval is then often further qualified using the terms like perfect, major, minor, augmented, or diminished in order to identify the interval quality. For example, a Major Second interval is typically two semi-tones, where each semi-tone is defined as a half-step or one-twelfth of an octave. A Perfect 4th is five semi-tones, a Perfect $5^{th}$ (or invented Perfect $4^{th}$) is seven semi-tones, and a Perfect 8th, or octave, is twelve semi-tones. In other cultures, quarter tones are incorporated into use of semitones and various exotic scales. While each of the harmonic intervals 4, 6 shown in FIG. 1 is illustrated as a Perfect 5th interval, a variety of other intervals may also be used. Three or more notes which are played simultaneously are typically referred to as a chord. Chords are typically named for how many notes they contain and the intervals from which they are constructed. For example, a Seventh ("7th") chord contains the basic triad—root, third, fifth—plus the descriptive added fourth note/tone, the seventh. There are various types of Seventh (7th) chords depending upon the quality of the original chord and the quality of the seventh which is added. For example, the harmonic intervals 4 and 6 which are shown in FIG. 1 illustrate a Major Seventh ($M7^{th}$) chord. In a diatonic context, the seventh note or tone of the major scale is the leading-tone of the scale, which has a strong tendency to pull for the tonal center, or root note, of the key. In music theory, the key identifies the tonic triad and the Perfect 5th is a representation of the fifth note in that key. Although FIG. 1 illustrates harmonic intervals which are Perfect 5ths in the key of C, any other keys or semitones may also be employed as the root with the appropriate intervals and structure. However, the specific notes shown here are the tones that are generally closest in frequency to the human voice for maximum therapeutic benefit.

The intervals illustrated in FIG. 1 may be provided in a variety of musical tunings, including equal temperament, schismatic temperament, meantone temperament, regular temperament, well temperament, Lucy tuning, Pythagorean tuning, Just Intonation, micro-tuning and others. However, the directly divisible ratios on which Just Intonation are based are what the human body recognizes as the most therapeutic, consonant and compelling frequency ratios. An interval that is tuned in this way is referred to as a just interval. For example, in one embodiment, the notes illustrated in FIG. 1 may be tuned as follows: C at 132 hertz, E at 165 hertz, G at 198 hertz, and B at 247.5 hertz. Although these frequencies are based on the modern conventionally accepted A=440 hertz, other base frequencies or Concert Pitches may also be used.

Figure 2:
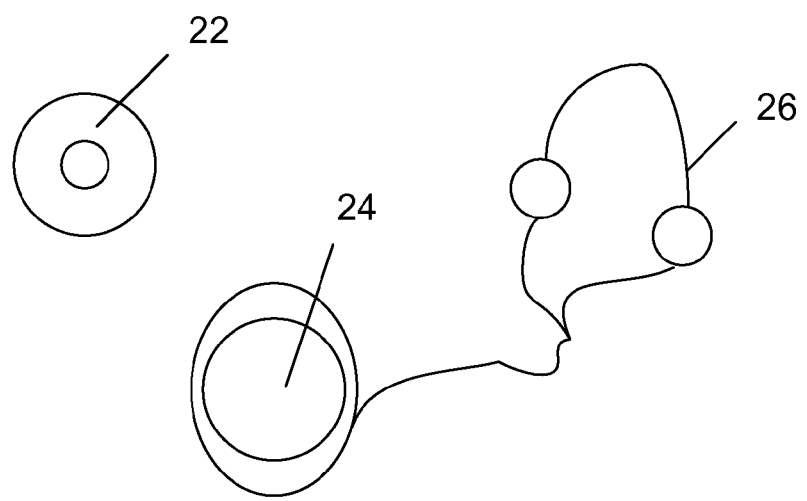
FIG. 2 is a sounding device including a sound recording for treating Autistic Spectrum Disorder and/or related emotional and physiological disorders.

FIG. 2 illustrates one technique for sounding the harmonic intervals, 4 and 6 shown in FIG. 1. In FIG. 2, the therapeutic method 2 (from FIG. 1) is recorded on a compact disc 22 or other recording medium, which is then played in a compact disc player 24 for a patient wearing headphones 26, or other sound generating, or sounding, device. Of course, a wide variety of other recording mediums and/or sounding devices may also be used, including, but not limited to, live performances, records, tapes (including digital audio tapes), digital recorders, loudspeakers, vocalizations, musical instruments, and/or tuning forks. For example, aluminum alloy tuning fork sounding devices produce the harmonics and the overtones which are the richest and warmest for best therapeutic results. The sound produced by those tuning forks, and/or other sounding devices, are recorded and enhanced using techniques available from Sandeep Salva of Atlanta, Ga. for minimizing the attack and decay of the tone, while sustaining the quality of the overtones and the harmonics without losing the character, the tone, the harmonics, the overtone, and the integrity of the notes.

While working with infants and children of various ages, the applicant has observed that the Perfect 5th interval and Major Seventh ($M7^{th}$) chords have a positive affect on well-being. These positive affects are caused by sympathetic resonance in the areas of the brain that release endorphins, such as the pituitary gland. In addition, the sympathetic vibrations also stimulate higher brain centers, such as the pituitary, penial, hypothalamus, thalamus, and amygdala, which scan incoming sound(s) for emotional content. Subsequently, this stimulates the brain stem, which includes the medulla oblongata, pons and mid-brain limbic region, the transition point between the body and the brain. These areas of the brain regulate not only the physical body, but sensory and emotional perceptions as well.

Only in Just Intonation does the Perfect $5^{th}$ create an exact vibrational ratio of 3:2, also referred to as "The Golden Ratio." Mathematical proportions, known as Pythagorean Tunings, create an archetypal resonance within the inner ear by stimulating the cochlea and the semi-circular canals. Because Fifths in Pythagorean Tuning are in the exact ratio of 3:2, they simultaneously provide harmonics and overtones, which are a direct result of the fundamental (first) note. The first harmonic overtone (the "partial"), vibrates exactly twice as fast as the first note, the second three times as fast as the first, and so on. When two tuning forks vibrate together, this creates a pattern containing at least two vibrational frequencies. Consequently, the brain hears not only the two frequencies, but also a third frequency—the actual difference between the two frequencies.

When multiple tuning forks vibrate together, a multitude of different frequencies, plus all of the resulting harmonics and overtones, administer a complex "sound bath," thereby synchronizing both hemispheres of the brain. Rhythm is processed by the left hemisphere, while harmony and intonation are processed by the right hemisphere. The convergent zones, which function in the prefrontal lobes, control attention span, judgment, impulse control and motivation. This is where the interconnectivity of the two hemispheres takes place, arousing complex and coordinated thought and emotional patterns.

Unfortunately, when those with Autism Spectrum Disorder and Asperger's Syndrome attempt to concentrate, their frontal lobes actually decrease in function. Nonetheless, the frontal lobes can be stimulated to process vibration. For example, the following cycle of brainwave frequencies are represented by Hz (cycles per second): 1) Beta (12-23 Hz)—normal waking state, 2) Alpha (8-12 Hz)—relaxed mind and body accelerated learning, 3) Theta (4-8 Hz)—a tranquil state of mind-body healing and 4) Delta (0.5-4 Hz)—deep sleep. Each of these states produces a unique pattern of electromagnetic brain waves representing the electrical and chemical activities of the brain.

The resulting immediate, compounded and accumulated long-term benefits of the audio therapy discussed and notated herein include, but are not limited to the following: 1) increasing the speed of brain synapses, 2) enhancing communication of neural networks, 3) stimulating consumption of glucose, resulting in greater overall brain activity, 4) inspiring intuition and creativity, 5) enriching motor coordination, 6) quickening pattern recognition, 7) expanding aural stimulation and 8) prolonging concentration, focus and memory.

It should be emphasized that the embodiments described above, and particularly any "preferred" embodiments, are merely examples of various implementations that have been set forth here to provide a clear understanding of various aspects of this technology. One of ordinary skill will be able to alter many of these embodiments without substantially departing from the scope of protection defined solely by the proper construction of the following claims.

What is claimed is:

1. A therapeutic method for treating autism spectrum disorder (ASD) and related disorders in a patient, comprising the steps of:
    playing a first harmonic interval for a first duration of at least approximately one minute, wherein the patient having ASD or a related disorder listens to the first harmonic interval on a sound generation device; and
    playing a second harmonic interval for a second, consecutive duration of at least approximately one minute, wherein the patient having ASD or a related disorder listens to the second harmonic interval on a sound generation device;
    wherein listening to the first and second harmonic intervals treats the patient's ASD or related disorder by at least one selected from the group consisting of: increasing the speed of brain synapses; enhancing the communication of the patient's neural networks; improving motor coordination; speeding up pattern recognition; and a combination thereof.

2. The method recited in claim 1, wherein the first and second harmonic intervals are fifths.

3. The method in claim 2, wherein the first and second harmonic intervals are just intervals.

4. The method recited in claim 2, wherein the fifths are Perfect 5ths.

5. The method in claim 4, wherein the first and second harmonic intervals are just intervals.

6. The method recited in claim 4, wherein the first duration overlaps with the second duration.

7. The method recited in claim 6, wherein the overlap of the first and second duration consequently sounds a Major Seventh (M7th) chord.

8. The method in claim 7, wherein the first and second harmonic intervals are just intervals.

9. The method recited in claim 7, wherein the first duration is at least approximately twenty minutes, the second duration is at least approximately ten minutes, and the overlap between the first and second duration is also at least approximately ten minutes.

10. The method in claim 9, wherein the first and second harmonic intervals are just intervals.

11. The method recited in claim 1, wherein listening to the first and second harmonic intervals treats the patient's ASD or related disorder by increasing the speed of brain synapses.

12. The method recited in claim 1, wherein listening to the first and second harmonic intervals treats the patient's ASD or related disorder by enhancing the communication of the patient's neural networks.

13. The method recited in claim 1, wherein listening to the first and second harmonic intervals treats the patient's ASD or related disorder by improving motor coordination.

14. The method recited in claim 1, wherein listening to the first and second harmonic intervals treats the patient's ASD or related disorder by speeding up pattern recognition.

15. A therapeutic method for treating autism spectrum disorder (ASD) and related disorders in a patient, comprising the step of:
    playing the notes B, C, E and G simultaneously for a duration of at least approximately ten minutes, wherein the patient having ASD or a related disorder listens to the notes on a sound generation device;
    wherein listening to the notes treats the patient's ASD or related disorder by at least one selected from the group consisting of: increasing the speed of brain synapses; enhancing the communication of the patient's neural networks; improving motor coordination; speeding up pattern recognition; and a combination thereof.

16. The method recited in claim 15, wherein listening to the notes treats the patient's ASD or related disorder by increasing the speed of brain synapses.

17. The method recited in claim 15, wherein listening to the notes treats the patient's ASD or related disorder by enhancing the communication of the patient's neural networks.

18. The method recited in claim 15, wherein listening to the notes treats the patient's ASD or related disorder by improving motor coordination.

* * * * *